US00PP34660P2

(12) United States Plant Patent
Sidhu

(10) Patent No.: US PP34,660 P2
(45) Date of Patent: Oct. 18, 2022

(54) ***PIERIS* PLANT NAMED 'PIESID2'**

(50) Latin Name: *Pieris japonica*
Varietal Denomination: Piesid2

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 17/709,911

(22) Filed: Mar. 31, 2022

(30) Foreign Application Priority Data

Apr. 15, 2021 (CA) ..... CA 21-10460

(51) Int. Cl.
*A01H 5/02* (2018.01)
*A01H 6/36* (2018.01)

(52) U.S. Cl.
USPC ..... Plt./226
CPC ..... *A01H 6/36* (2018.05)

(58) Field of Classification Search
USPC ..... Plt./226
CPC ..... A01H 6/36; A01H 5/02
See application file for complete search history.

*Primary Examiner* — Keith O. Robinson
(74) *Attorney, Agent, or Firm* — Penny J. Aguirre

(57) ABSTRACT

A new cultivar of *Pieris* plant named 'Piesid2' that is characterized by its foliage with new growth that is vibrant red in color, its dense globose to rounded plant habit, and its flowers that are white and heavily flushed with pink.

2 Drawing Sheets

Botanical classification: *Pieris japonica.*
Cultivar designation: 'Piesid2'.

CROSS REFERENCE TO A RELATED APPLICATION

This application claims priority to a Canadian Plant Breeder's Rights Application No. 21-10460 filed on Apr. 15, 2021, under 35 U.S.C. 119(f), the entire contents of which is incorporated by reference herein.

BACKGROUND OF THE INVENTION

The present invention relates to a new and distinct cultivar of *Pieris japonica* and will be referred to hereafter by its cultivar name, 'Piesid2'. 'Piesid2' represents a new Japanese andromeda; an evergreen shrub grown for landscape use.

The inventor discovered 'Piesid2' as a naturally occurring branch mutation of *Pieris japonica* 'Valley Rose' (not patented) in summer of 2016 that was growing outdoors in a container in a production block in Mission, B.C., Canada.

Asexual propagation of the new cultivar was first accomplished by tissue culture using meristematic tissue by the Inventor in spring of 2018 in Mission, B.C., Canada. Asexual propagation by tissue culture has determined that the characteristics of the new cultivar are stable and are reproduced true to type in successive generations.

SUMMARY OF THE INVENTION

The following traits have been repeatedly observed and represent the characteristics of 'Piesid2'. These attributes in combination distinguish 'Piesid2' as a new and distinct cultivar of *Pieris.*

1. 'Piesid2' exhibits foliage with new growth that is vibrant red in color.

2. 'Piesid2' exhibits a dense globose to rounded plant habit.
3. 'Piesid2' exhibits flowers that are white and heavily flushed with pink.

The parent plant of 'Piesid2' is similar to 'Piesid2' in having plant habit and flower color but differs from 'Piesid2' in having new foliage growth that is bronze in color. 'Piesid2' can also be most closely compared to *Pieris japonica* 'Mountain Fire' (not patented). 'Mountain Fire' is similar to 'Piesid2' in plant habit and in having new foliage growth that is red in color. 'Mountain Fire' differs from 'Piesid2' in having flowers that are pure white in color and lack any pink coloration.

BRIEF DESCRIPTION OF THE DRAWINGS

The accompanying color photographs illustrate the overall appearance and distinct characteristics of the new *Pieris*. The photographs were taken of a 3-year-old plant of the new cultivar as grown outdoors in a 1-gallon container in St. Thomas, Ontario, Canada.

The photograph in FIG. 1 provides a side view of 'Piesid2' in spring.

Figure 1:
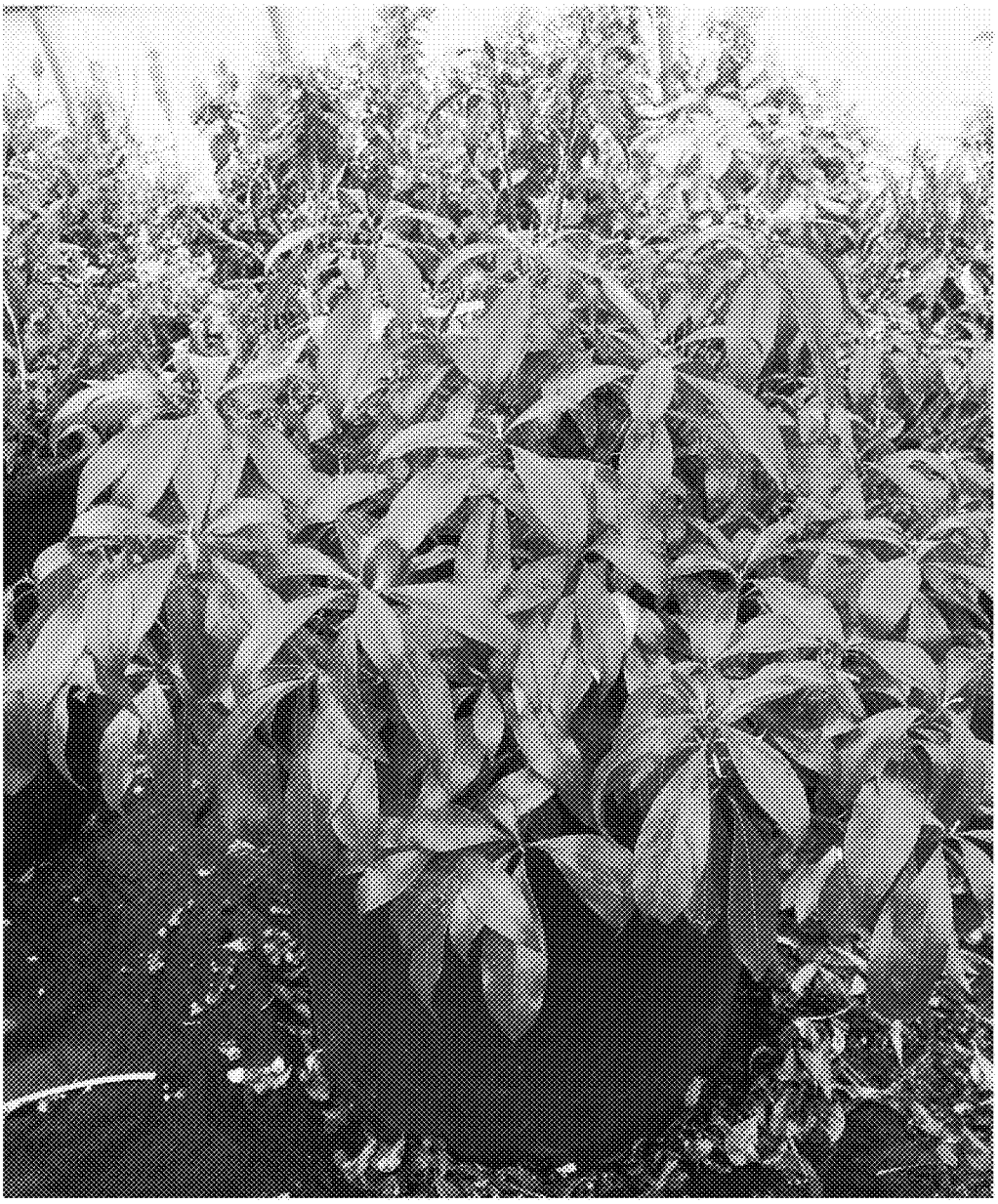
Figure 2:
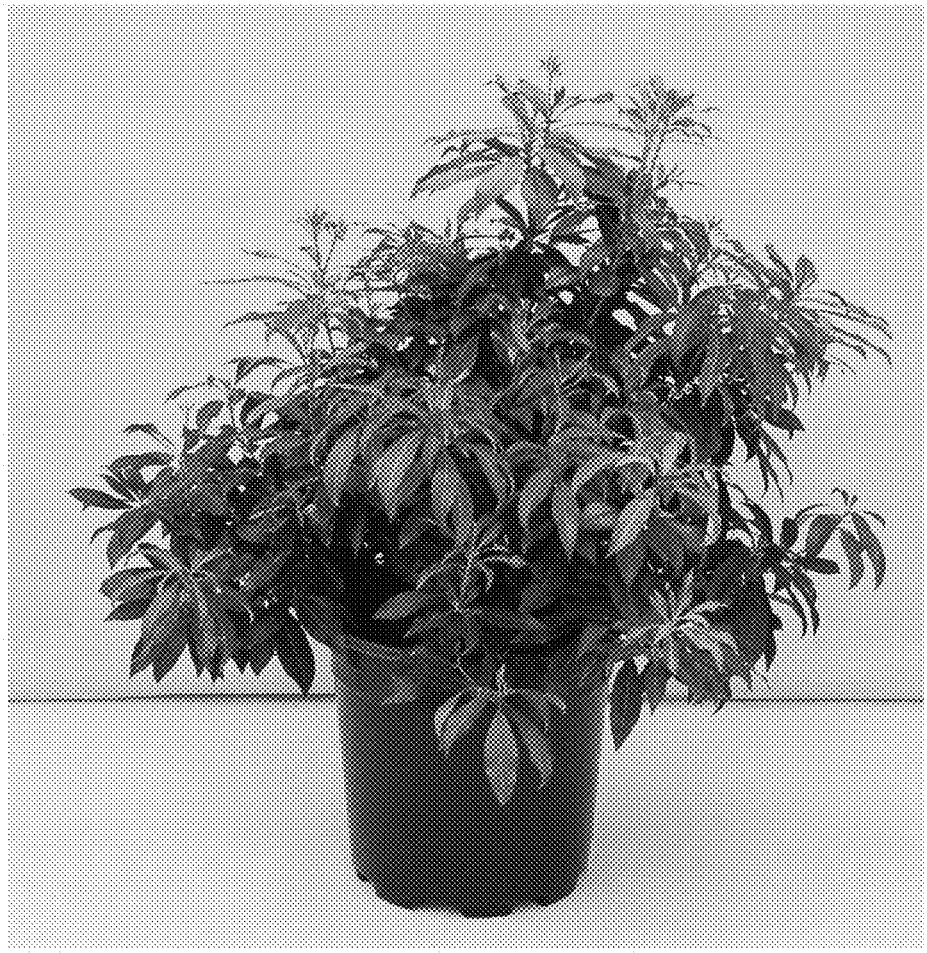

The photograph in FIG. 2 provides a close-up view of the new and mature foliage of 'Piesid2'.

Figure 3:
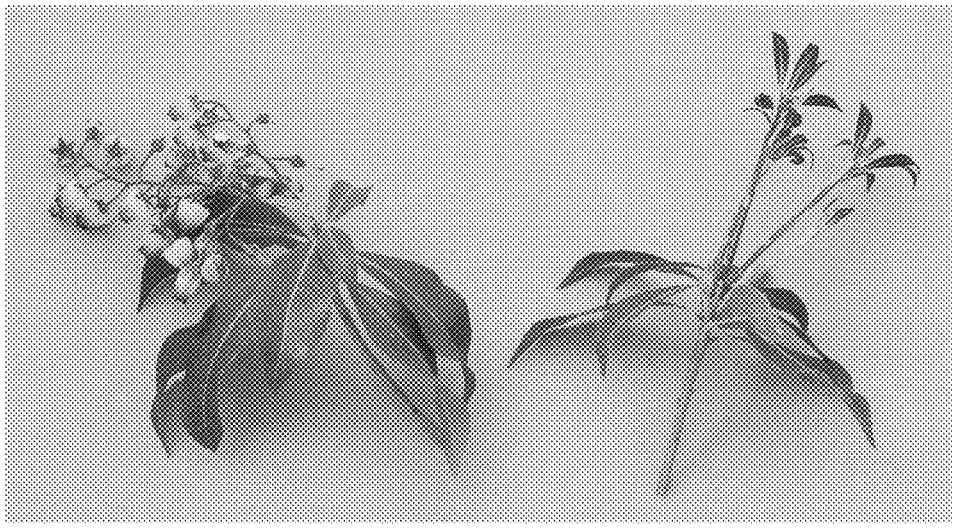

The photograph in FIG. 3 provides a close-up view of the flowers (left) and new growth (right).

The colors in the photographs are as close as possible with the digital photography and printing techniques utilized and the color codes in the detailed botanical description accurately describe the new *Pieris.*

DETAILED BOTANICAL DESCRIPTION OF THE PLANT

The following is a detailed description of 3-year-old plants of the new cultivar as grown outdoors in 1-gallon containers in St. Thomas, Ontario, Canada. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General characteristics:

*Blooming period.*—March through April in British Columbia, Canada.

*Plant habit.*—Broadleaf evergreen shrub.

*Plant habit.*—Dense, globose to mounded.

*Height and spread.*—An average of 40 cm in height and 53 cm in spread (1-gallon container), mature plant in the landscape an average of 1.52 m in height, 1.22 m in spread.

*Hardiness.*—Heat tolerance to U.S.D.A. Zone 8b to cold hardiness to Zone 6.

*Diseases and pests.*—Good resistance has been observed for root rot typically caused by *Phytophthora cactorum* and leaf spot typically caused by *Alternaria alternata, Pestalotia* sp., or *Phyliosticta* sp., no resistance or susceptibility to pests has been observed.

*Root description.*—Fibrous.

*Propagation type.*—Tissue culture.

*Root development.*—Time required for root initiation; 6 weeks from tissue culture, and 2 growing seasons to produce a fully rooted 1-gallon plant.

*Growth rate.*—Moderate, but less vigorous than is typical for most plants of *Pieris japonica.*

Branch description:

*Branch color.*—New growth; 144D, flushed with 60B, irregularly streaked with 144D. mature wood; a blend of 177A and 177B.

*Branch shape.*—Oval.

*Branch size.*—Main stem; average of 12 cm in length and 1 cm in width, lateral branches an average of 25 cm in length and 7 mm in width in center of branch.

*Branch surface.*—Glabrous and slightly ridged.

*Branching.*—Moderately branched; an average of 3 lateral branches each with an average 4 secondary branches.

*Vegetative buds.*—Stem surface sparsely covered with vegetative buds, average of 1 mm in diameter, 177A in color, flushed with 60B, irregularly streaked with 144D.

Foliage description:

*Leaf shape.*—Elliptic to oblanceolate.

*Leaf division.*—Simple.

*Leaf base.*—Cuneate.

*Leaf apex.*—Acute to acuminate.

*Leaf venation.*—Pinnate, only midrib is conspicuous; 145B on upper surface, 145C on lower surface.

*Leaf margin.*—Entire with distal portion weakly serrate.

*Leaf attachment.*—Petiolate.

*Leaf arrangement.*—Spiral, whorl-like.

*Leaf surface.*—Both surfaces glossy, glabrous, finely puberulent along midrib.

*Leaf texture.*—Both surfaces leathery.

*Leaf size.*—An average of 9 cm in length and 2.9 cm in width.

*Leaf quantity.*—Average of 30 per branch, per a branch 18 cm in length.

*Internode length.*—An average of 2 mm on upper of branch and 1.5 cm on lower branch.

*Leaf color.*—Young upper surface; 187B in the spring, 45C in summer, young lower surface; 187B to 187C in spring, 29C in summer, mature upper surface; NN137A, mature lower surface; NN137B to NN137C.

*Petioles.*—Average of 9 mm in length, 2 mm in width, NN137B in color, surface glabrous.

*Stipules.*—None.

*Leaf buds in leaf axils.*—1 cm in length and 2 mm in diameter; surface 160B in color.

Flower description:

*Inflorescence type.*—Terminal paniculate racemes.

*Inflorescence size.*—Average of 11 cm in length and width.

*Inflorescence lastingness.*—3 to 4 weeks.

*Inflorescence quantity.*—Up to 10 per plant.

*Flower type.*—Urceolate.

*Flower fragrance.*—Light and pleasant.

*Flower bud description.*—Buds are formed the previous season, ovate in shape, about 6 mm in length and 4 mm in width, a blend of N186C to N186D in color prior to flower opening.

*Flower quantity.*—Average of 25 flowers per raceme branch, an average of 125 per inflorescence.

*Flower size.*—Average of 8 mm in depth and diameter.

*Rachis.*—Branches are about 7 cm in length and 1 mm in width, N186C and lower (non-sunny side) may be more green than 160A.

*Pedicels.*—Average of 8 mm in length and 1 mm in diameter, 184D in color.

*Petal description.*—5, oblong in shape, base fused with very apex un-fused and acute in shape, dentate and slightly reflexed, upper and lower surface is glabrous, NN155B, apex 72C, N77A along apex margin, corolla size is an average of 8 mm in length and diameter with free tip portion an average of 1 mm in length and diameter.

*Calyx.*—Rotate-like, average of 4 mm in height and 9 mm in diameter.

*Sepal description.*—5, lanceolate in shape, margin is entire, apex is acute, surface is glabrous on upper and lower surface, an average of 4 mm in length and 1.5 mm in width, color; a blend of 53C and 162C.

Reproductive organs:

*Gynoecium.*—Pistil; 1, 7 mm in length, stigma; globular in shape, 59A in color, style; 6.9 mm in length, 8C in color, ovary; 59A in color.

*Androecium.*—Stamens; 5, anthers; oblong in shape, about 1 mm in length and 161A in color, 2 hairs extending from anthers about 0.5 mm in length and 177B in color, pollen; abundant and NN155C in color.

*Fruit and Seed.*—5-valved capsules persist throughout the year on the fruiting stalks, ornamentally insignificant, average of 3 mm in length, 1 mm in width, 166A in color, seed was not discernable.

It is claimed:

1. A new and distinct cultivar of *Pieris* plant named 'Piesid2' as herein illustrated and described.

* * * * *